US010314521B2

(12) United States Patent
Jagannathan et al.

(10) Patent No.: US 10,314,521 B2
(45) Date of Patent: Jun. 11, 2019

(54) USER CONDITION EVALUATION SYSTEM THROUGH TOUCH SCREEN DEVICE USAGE PATTERN CHANGE

(71) Applicant: International Business Machines Corporation, Armonk, NY (US)

(72) Inventors: Harini Jagannathan, San Jose, CA (US); Fang Lu, Billerica, MA (US); Anca Sailer, Scarsdale, NY (US); Chin Ngai Sze, Austin, TX (US); Jingwei Yang, Cambridge, MA (US)

(73) Assignee: International Business Machines Corporation, Armonk, NY (US)

( * ) Notice: Subject to any disclaimer, the term of this patent is extended or adjusted under 35 U.S.C. 154(b) by 20 days.

(21) Appl. No.: 15/708,322

(22) Filed: Sep. 19, 2017

(65) Prior Publication Data

US 2019/0083006 A1 Mar. 21, 2019

(51) Int. Cl.
*A61B 5/00* (2006.01)
*A61B 5/11* (2006.01)
(Continued)

(52) U.S. Cl.
CPC .......... *A61B 5/1124* (2013.01); *A61B 5/0022* (2013.01); *A61B 5/1101* (2013.01); *A61B 5/4082* (2013.01); *A61B 5/6897* (2013.01); *G06F 3/04883* (2013.01); *G06N 5/046* (2013.01); *G09B 5/02* (2013.01);
(Continued)

(58) Field of Classification Search
CPC ... A61B 5/4076; A61B 5/4082; A61B 5/4088; A61B 5/4094; A61B 5/16–5/18; A61B 5/4058; A61B 5/4064; A61B 5/407; G06F 3/0412; G06F 3/0414; G06F 3/04883; G06F 3/0488; G06F 2203/04105
See application file for complete search history.

(56) References Cited

U.S. PATENT DOCUMENTS 6,546,134 B1 4/2003 Shrairman
7,280,679 B2 10/2007 Russo
(Continued)

FOREIGN PATENT DOCUMENTS

| CN | 104586403 A | 5/2015 |
|---|---|---|
| WO | 2017042767 A1 | 3/2017 |
| WO | 2017044092 A1 | 3/2017 |

OTHER PUBLICATIONS

Arroyo-Gallego, et al. "Detection of Motor Impairment in Parkinson's Disease via Mobile Touchscreen Typing." IEEE Transactions on Biomedical Engineering, vol. 64, No. 9, Sep. 2017, pp. 1994-2002.
(Continued)

*Primary Examiner* — Adam J Eiseman
(74) *Attorney, Agent, or Firm* — Andrew Aubert; David Woycechowsky (57) ABSTRACT

Technology for use with a touchscreen user interface device that uses gesture swipe data to provide an early potential indication of onset of Parkinson's disease. Technology for use with a touchscreen user interface device that uses gesture swipe data to provide an information about motor skill development of a child. Technology for use with a touchscreen user interface device that uses gesture swipe data to provide an information about reading ability development of a child.

17 Claims, 5 Drawing Sheets

(51) Int. Cl.
    *G06F 3/0488* (2013.01)
    *G06N 5/04* (2006.01)
    *G09B 5/02* (2006.01)
    *G09B 17/00* (2006.01)
    *G16H 50/20* (2018.01)

(52) U.S. Cl.
    CPC .......... *G09B 17/003* (2013.01); *G16H 50/20* (2018.01); *A61B 2503/06* (2013.01)

(56) References Cited

U.S. PATENT DOCUMENTS

| | | | |
|---|---|---|---|
| 9,264,903 | B2 | 2/2016 | Pratt |
| 9,883,831 | B1 | 2/2018 | Stewart |
| 9,895,085 | B2 | 2/2018 | Davis |
| 2012/0330182 | A1 | 12/2012 | Alberts |
| 2014/0028575 | A1 | 1/2014 | Parivar |
| 2014/0336539 | A1 | 11/2014 | Torres |
| 2015/0272504 | A1* | 10/2015 | Giancardo .......... A61B 5/7267 600/595 |
| 2016/0073945 | A1 | 3/2016 | Fine |
| 2016/0085921 | A1 | 3/2016 | Farrell et al. |
| 2016/0140317 | A1 | 5/2016 | Bowers |
| 2017/0025033 | A1 | 1/2017 | Rath |

OTHER PUBLICATIONS

Jagannathan, et al., "User Condition Evaluation System Through Touch Screen Device Usage Pattern Change", U.S. Appl. No. 15/841,358, filed Dec. 14, 2017.

List of IBM Patents or Patent Applications Treated as Related. Filed Dec. 14, 2017, 2 pages.

A4CWSN, "Dextera Dots 2", Apps for Children with Special Needs, Dr. Brown's Apps, Autism DTT Pro, Aug. 12, 2014, 5 pages.

A4CWSN, "Dextera Dots 2", Apps for Children with Special Needs, Fine Motor, Apps for Speech Therapy, Mobile Education Store, Aug. 12, 2014, 7 pages.

Arroyo-Gallego et al., "Detection of Motor Impairment in Parkinson's Disease via Mobile Touchscreen Typing", This article has been accepted for publication in a future issue of this journal, but has not been fully edited. Content may change prior to final publication. Citation information: DOI 10.1109/TBME.2017.2664802, IEEE Transactions on Biomedical Engineering, 0018-9294 (c) 2016 IEEE, 9 pages.

Crescenzi et al., "The role of touch in preschool children's learning using iPad versus paper interaction", Australian Journal of Language and Literacy, vol. 37, No. 2, 2014, pp. 86-95.

Eng, Karen, "mPowering the Apple Research Kit: How Max Little put a Parkinson's app on the iPhone", Mar. 13, 2015, 8 pages, <http://blog.ted.com/how-max-little-put-a-parkinsons-app-on-the-iphone/>.

Kelly, Kate, "Fine Motor Skills: What You Need to Know", downloaded from the internet on Aug. 23, 2017, <https://www.understood.org/en/learning-attention-issues/child-learningdisabilities/movement-coordination-issues/all-about-fine-motor-skills>, 3 pages.

Macrae, Fiona, "Now smartphones can diagnose Parkinson's by recording a person's voice and movements", The Daily Mail, Sep. 8, 2014, 6 pages.

Morin, Amanda, "Coordination and Motor Skills: What to Expect at Different Ages", Understood, downloaded from the internet Aug. 23, 2017, 7 pages, <https://www.understood.org/en/learning-attention-issues/signs-symptoms/age-by-age-learning-skills/coordination-and-motor-skills-what-to-expect-at-different-ages>.

Sage Bionetworks, a Not-For-Profiit Research Organization, "Parkinson mPower study app", Mar. 18, 2017, Version 1.4.1, 3 pages, <https://itunes.apple.com/us/app/parkinson-mpower-study-app/id972191200?mt=8>.

Sole-Casals et al., "A Preliminary Review of Behavioural Biometrics for Health Monitoring in the Elderly", provided in Post Disclosure Comments dated Dec. 14, 2016, 7 pages.

Van Den Eeden et al., "Incidence of Parkinson's Disease: Variation by Age, Gender, and Race/Ethnicity", American Journal of Epidemiology, vol. 157, No. 11, Printed in U.S.A., DOI: 10.1093/aje/kwg068, Received for publication Dec. 28, 2001; accepted for publication Nov. 27, 2002, pp. 1015-1022.

* cited by examiner

FIG. 6

USER CONDITION EVALUATION SYSTEM THROUGH TOUCH SCREEN DEVICE USAGE PATTERN CHANGE

BACKGROUND

The present invention relates generally to the field of health-related data collection devices, and more particularly to the field of devices for collection of data related to hand movement and/or musculature. Touch screens are used more and more often by all different age of groups of people. People use the touch screen devices for various purposes, such as reading, emailing, chatting and making phone calls.

As stated at the Abstract of the article "Detection of Motor Impairment in Parkinson's Disease via Mobile Touchscreen Typing" by Teresa Arroyo-Gallego et al. (published by IEEE, 2016) "Mobile technology is opening a wide range of opportunities for transforming the standard of care for chronic disorders. Using smartphones as tools for longitudinally tracking symptoms could enable personalization of drug regimens and improve patient monitoring. Parkinson's disease (PD) is an ideal candidate for these tools. At present, evaluation of PD signs requires trained experts to quantify motor impairment in the clinic, limiting the frequency and quality of the information available for understanding the status and progression of the disease. Mobile technology can help clinical decision making by completing the information of motor status between hospital visits. This paper presents an algorithm to detect PD by analyzing the typing activity on smartphones independently of the content of the typed text. We propose a set of touchscreen typing features based on a covariance, skewness and kurtosis analysis of the timing information of the data to capture PD motor signs . . . . This work contributes to the development of a home-based, high-compliance and high-frequency PD motor test by analysis of routine typing on touchscreens."

SUMMARY

According to an aspect of the present invention, there is a method, computer program product and/or system for use with a touchscreen user interface device that performs the following operations (not necessarily in the following order): (i) receiving a Parkinson's Disease (PD) potential indication module including a set of machine logic based rules for determining when changes in gesture swipe patterns of touchscreen gesture instances correspond to a potential indication of early onset of PD; (ii) receiving a plurality of touchscreen gesture data sets, with each touchscreen gesture data set including information indicative of: (a) the geometry of an instance of a gesture swipe made by a user on the touchscreen user interface device, and (b) a time that the instance of the touchscreen gesture swipe occurred; (iii) detecting a first change in geometry of the user's gestures over time by comparing touchscreen gesture data sets of the plurality of touchscreen gesture data sets with each other; (iv) applying the machine logic based rules of the PD potential indication module to determine that the detection of the first change in geometry corresponds to a potential indication of PD; and (v) sending a communication indicating a potential indication of PD for the user.

According to an aspect of the present invention, there is a method, computer program product and/or system for use with a touchscreen user interface device that performs the following operations (not necessarily in the following order): (i) receiving a child motor skills module including a set of machine logic based rules for mapping changes in gesture patterns of touchscreen gesture instances to information about development of motor skills of children; (ii) receiving a plurality of touchscreen gesture data sets, with each touchscreen gesture data set including information indicative of: (a) how spatially accurate a gesture was made relative to a gesture target, and (b) a time that the instance of the touchscreen gesture occurred; (iii) detecting a first change in accuracy of the user's gestures over time by comparing touchscreen gesture data sets of the plurality of touchscreen gesture data sets with each other; (iv) applying the machine logic based rules of the child motor skills module to determine corresponding information about motor development of the user based upon the first change in accuracy; and (v) sending a communication indicating the information about motor development of the user.

According to an aspect of the present invention, there is a method, computer program product and/or system for use with a touchscreen user interface device that performs the following operations (not necessarily in the following order): (i) receiving a reading skills module including a set of machine logic based rules for mapping changes in gesture patterns of touchscreen gesture instances to information about development of reading skills of children; (ii) receiving a plurality of touchscreen gesture data sets, with each touchscreen gesture data set including reading speed information indicative of how quickly successive gestures served to scroll through portions of respectively associated text(s); (iii) detecting a first change in reading speed by comparing touchscreen gesture data sets of the plurality of touchscreen gesture data sets with each other; (iv) applying the machine logic based rules of the reading skills module to determine corresponding information about the user's reading skills; and (v) sending a communication indicating the information about reading skills of the user.

DETAILED DESCRIPTION

In some embodiments, a touchscreen user interface device uses gesture swipe data (for example, transverse discontinuities in swipes) to provide an early potential indication of onset of Parkinson's disease. A communication of this potential indication may be sent to the user who made the swipes and/or to an appropriated medical entity so that any appropriate Parkinson's disease testing may be conducted in response to the indication. In some embodiments, a touchscreen user interface device uses gesture data to provide an information about motor skill development (for example, trace and tap accuracy) of a child. In some embodiments, a touchscreen user interface device uses gesture data to provide an information about reading ability development of a child. This Detailed Description section is divided into the following sub-sections: (i) The Hardware and Software Environment; (ii) Example Embodiment; (iii) Further Comments and/or Embodiments; and (iv) Definitions.

I. The Hardware and Software Environment

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 1:
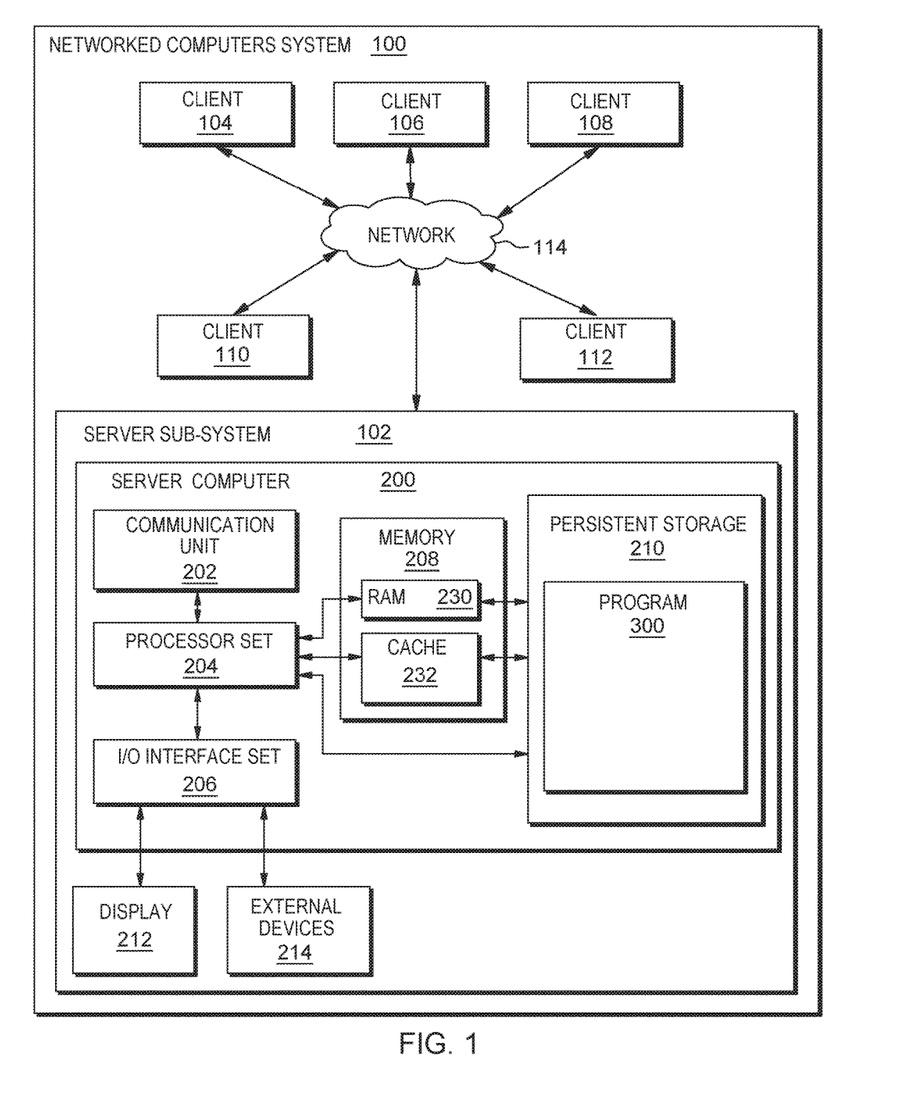
FIG. 1 is a block diagram view of a first embodiment of a system according to the present invention.

An embodiment of a possible hardware and software environment for software and/or methods according to the present invention will now be described in detail with reference to the Figures. FIG. 1 is a functional block diagram illustrating various portions of networked computers system 100, including: server sub-system 102; client sub-systems 104, 106, 108, 110, 112; communication network 114; server computer 200; communication unit 202; processor set 204; input/output (I/O) interface set 206; memory device 208; persistent storage device 210; display device 212; external device set 214; random access memory (RAM) devices 230; cache memory device 232; and program 300.

Sub-system 102 is, in many respects, representative of the various computer sub-system(s) in the present invention. Accordingly, several portions of sub-system 102 will now be discussed in the following paragraphs.

Sub-system 102 may be a laptop computer, tablet computer, netbook computer, personal computer (PC), a desktop computer, a personal digital assistant (PDA), a smart phone, or any programmable electronic device capable of communicating with the client sub-systems via network 114. Program 300 is a collection of machine readable instructions and/or data that is used to create, manage and control certain software functions that will be discussed in detail, below, in the Example Embodiment sub-section of this Detailed Description section.

Sub-system 102 is capable of communicating with other computer sub-systems via network 114. Network 114 can be, for example, a local area network (LAN), a wide area network (WAN) such as the Internet, or a combination of the two, and can include wired, wireless, or fiber optic connections. In general, network 114 can be any combination of connections and protocols that will support communications between server and client sub-systems.

Sub-system 102 is shown as a block diagram with many double arrows. These double arrows (no separate reference numerals) represent a communications fabric, which provides communications between various components of sub-system 102. This communications fabric can be implemented with any architecture designed for passing data and/or control information between processors (such as microprocessors, communications and network processors, etc.), system memory, peripheral devices, and any other hardware components within a system. For example, the communications fabric can be implemented, at least in part, with one or more buses.

Memory 208 and persistent storage 210 are computer-readable storage media. In general, memory 208 can include any suitable volatile or non-volatile computer-readable storage media. It is further noted that, now and/or in the near future: (i) external device(s) 214 may be able to supply, some or all, memory for sub-system 102; and/or (ii) devices external to sub-system 102 may be able to provide memory for sub-system 102.

Program 300 is stored in persistent storage 210 for access and/or execution by one or more of the respective computer processors 204, usually through one or more memories of memory 208. Persistent storage 210: (i) is at least more persistent than a signal in transit; (ii) stores the program (including its soft logic and/or data), on a tangible medium (such as magnetic or optical domains); and (iii) is substantially less persistent than permanent storage. Alternatively, data storage may be more persistent and/or permanent than the type of storage provided by persistent storage 210.

Program 300 may include both machine readable and performable instructions and/or substantive data (that is, the type of data stored in a database). In this particular embodiment, persistent storage 210 includes a magnetic hard disk drive. To name some possible variations, persistent storage 210 may include a solid state hard drive, a semiconductor storage device, read-only memory (ROM), erasable programmable read-only memory (EPROM), flash memory, or any other computer-readable storage media that is capable of storing program instructions or digital information.

The media used by persistent storage 210 may also be removable. For example, a removable hard drive may be used for persistent storage 210. Other examples include optical and magnetic disks, thumb drives, and smart cards that are inserted into a drive for transfer onto another computer-readable storage medium that is also part of persistent storage 210.

Communications unit 202, in these examples, provides for communications with other data processing systems or devices external to sub-system 102. In these examples, communications unit 202 includes one or more network interface cards. Communications unit 202 may provide communications through the use of either or both physical and wireless communications links. Any software modules discussed herein may be downloaded to a persistent storage device (such as persistent storage device 210) through a communications unit (such as communications unit 202).

I/O interface set 206 allows for input and output of data with other devices that may be connected locally in data communication with server computer 200. For example, I/O interface set 206 provides a connection to external device set 214. External device set 214 will typically include devices such as a keyboard, keypad, a touch screen, and/or some other suitable input device. External device set 214 can also include portable computer-readable storage media such as, for example, thumb drives, portable optical or magnetic disks, and memory cards. Software and data used to practice embodiments of the present invention, for example, program 300, can be stored on such portable computer-readable storage media. In these embodiments the relevant software may (or may not) be loaded, in whole or in part, onto persistent storage device 210 via I/O interface set 206. I/O interface set 206 also connects in data communication with display device 212.

Display device 212 provides a mechanism to display data to a user and may be, for example, a computer monitor or a smart phone display screen.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

II. Example Embodiment

Figure 2:
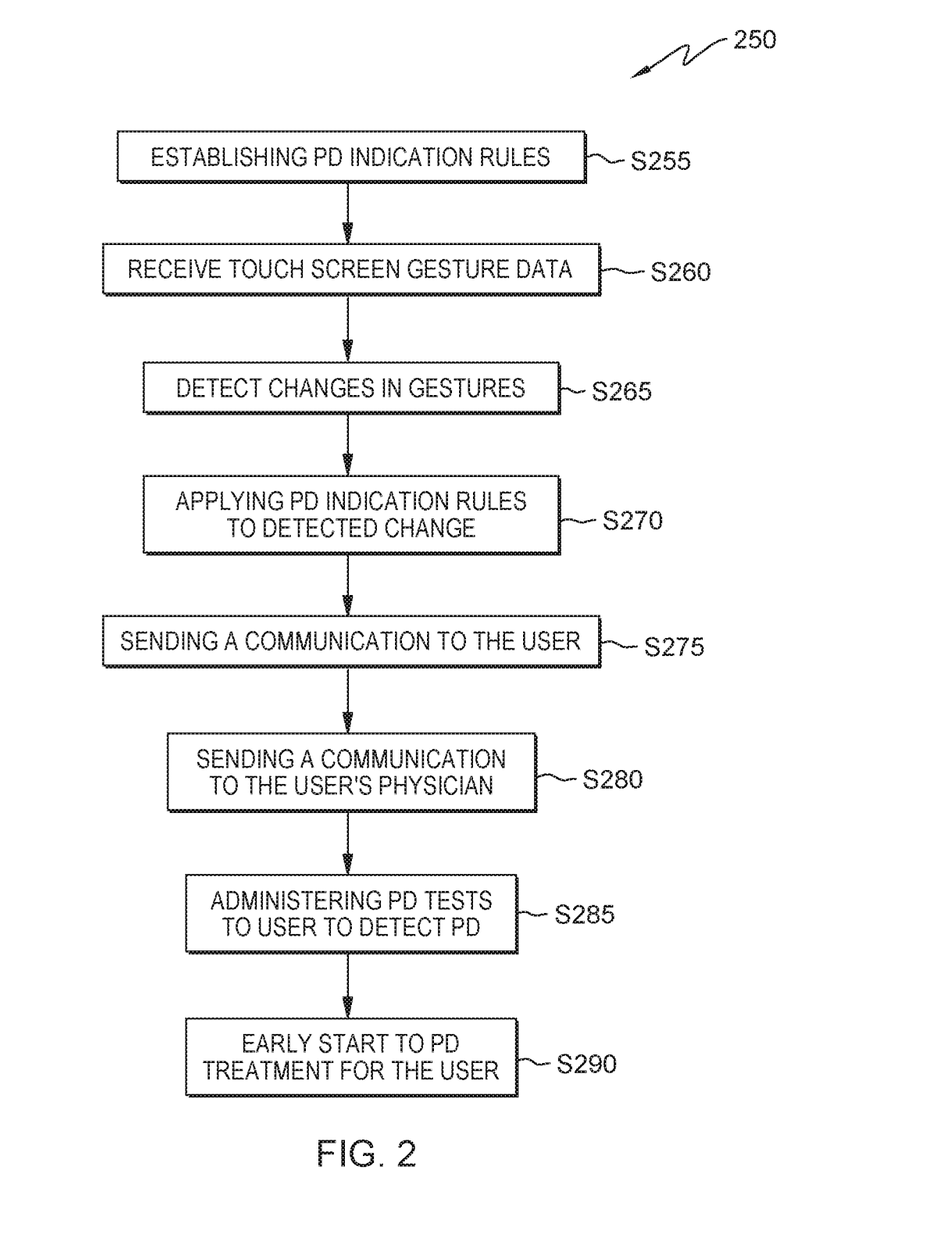
FIG. 2 is a flowchart showing a first embodiment method performed, at least in part, by the first embodiment system.
Figure 3:
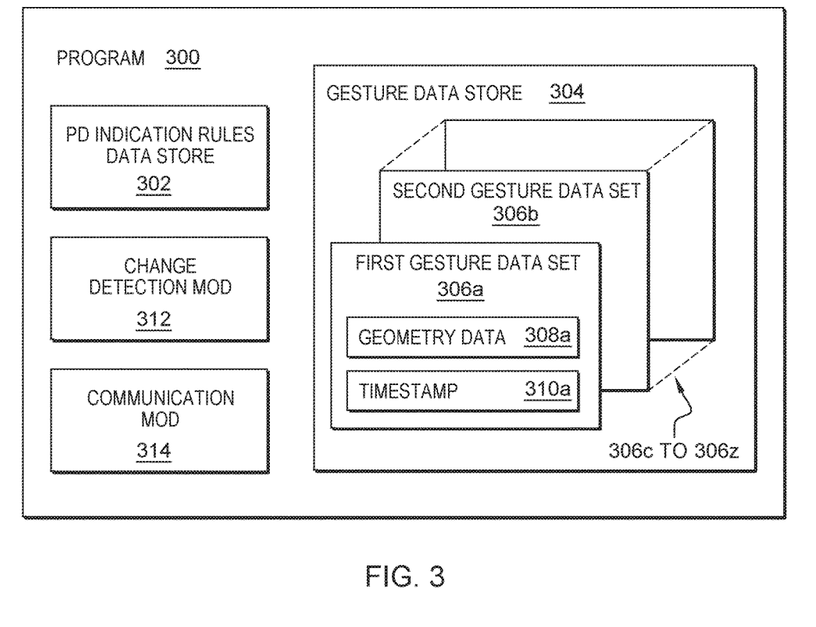
FIG. 3 is a block diagram showing a machine logic (for example, software) portion of the first embodiment system.

FIG. 2 shows flowchart 250 depicting a method according to the present invention. FIG. 3 shows program 300 for performing at least some of the method operations of flowchart 250. This method and associated software will now be discussed, over the course of the following paragraphs, with extensive reference to FIG. 2 (for the method operation blocks) and FIG. 3 (for the software blocks).

Processing begins at operation S255, where Parkinson's disease (PD) detection machine logic based rules are established by: (i) client sub-system 104 (see FIG. 1) generating the set of Parkinson's disease (PD) detection machine logic based rules; and (ii) client sub-system 104 sending the set of PD detection rules to PD indication rules data store 302 of program 300 over network 114. In this embodiment, the machine logic based rules are developed by a team of neurologists and software developers working co-operatively. Alternatively, these rules could be developed, in whole or in part, by machine learning, artificial intelligence and the like.

In this embodiment, the rules of data store 302 relate to early detection of incipient PD. Alternatively, these detection rules may relate to other aspects of neurological development, such as: (i) reading speed (for example, reading speed of child who has just started learning to read); and/or (ii) development of motor skills (for example, redevelopment of motor skills pursuant to stroke treatment).

Processing proceeds to operation S260, where client sub-systems 106, 108, 110 send "touchscreen gesture data sets" 306a to 306z, over network 114, to gesture data store 304 of program 300. In this embodiment, client sub-systems 106, 108 and 110 are smart phones owned and operated by three individuals who happen to be in the care of Dr. Good, a general practitioner of medicine. These data sets are generated when these individuals use their smart phones for everyday communication and/or computing tasks, such as emailing, chatting, browsing the web and/or participating in social media. Each of these touchscreen gesture data sets corresponds to a single "swipe" type gesture (see, definition of "gesture," below) that the individuals made. Swipe gestures define a longitudinal direction (lying in the plane of the touchscreen surface) and a transverse direction which is: (i) also in the plane of the touchscreen surface; but (ii) (or-thogonal to the longitudinal direction with respect to any given point in the path of the swipe. Alternatively, or additionally, other types of gestures could be tracked, such as tap type gestures. This embodiment tracks users during "normal operations" (see, definition of normal operations, below). Alternatively, or additionally, the gestures could be made on a dedicated touchscreen located in a doctor's office (such as client sub-system 112 (see FIG. 1), which is a special purpose tablet computer owned by Dr. Good and operated in his office by her professional staff).

More specifically, each touchscreen gesture data set 306a to 306z includes: (i) geometry data 308a to 308z that indicates the shape, or profile, of the linear path of the swipe; and (ii) timestamp data 310a to 310z that indicates the date and time. As will be explained further below, changes in geometry patterns (as determined by the geometry data) over time (as determined by the timestamp data) allows the machine logic rules to detect potential onset of PD at a relatively early stage. Alternatively, if other neurological phenomena are being detected (for example, motor skills, reading speed), then other physical characteristics of the gestures may be, alternatively or additionally, present. For example, in reading speed detection embodiments, the gesture data sets may include a reading difficulty value of text being read by a user that corresponds to a gesture (for example, user's gesture tracing words on the touchscreen as the user reads them).

Processing proceeds to operation S265 where change detection module 312 detects changes in in the geometry data corresponding to a single individual over time (as determined by the timestamp data corresponding to that individual). In this embodiment, the individual being checked for potential onset of PD is named Petunia and she is the person operating client sub-system 106 over a period of three months, sending gesture data sets to program 300 over network 114 during that time. The accumulated gesture data sets indicate changes in the geometry data consisting of an increase in the frequency and/or amplitude of transverse discontinuities in swipes relative to the longitudinal direction of the swipes. In this example, mod 312 determines: (i) during the first week of the three month period, Petunia's swipe type gestures, taken collectively (but throwing out outliers in order to account for possible phenomena such as swipes made in a moving subway cars or during small earthquakes), had an average of 0.334 transverse direction discontinuities per centimeter of swipe length; (ii) during the last week of the three month period, Petunia's swipe type gestures, taken collectively (again throwing out outliers), had an average of 1.564 transverse direction discontinuities per centimeter of swipe length; and (iii) a change in transverse direction discontinuities per centimeter of swipe length over the three month period as 1.230.

Alternatively, change detection module 312 could be programmed to detect changes in different gestures, such as: (i) consistency of pressure applied during pressure-sensitive gestures such as pressing a finger to a screen to verify the identity of a user via fingerprint analysis; (ii) accuracy in tracing patterns by touchscreen gesture to help determine development of fine motor skills in children; (iii) smaller handwriting relative to earlier examples of handwriting on a touchscreen; and/or (iv) changes in time periods between successive text-scrolling swipes connected to text portions having approximately the same reading level difficulty to determine development of reading skills in children.

Processing proceeds to operation S270 where change detection module 312 applies the PD indication rules from PD indication rules data store 302 to the detected changes to determine if an individual is a likely candidate for PD. In this embodiment, one of these rules specifies that if average discontinuities go up by greater than 1.000 in a three-month period then the individual should be brought in for PD onset detection setting with an urgency level of 0.75 (which is a relatively high level of urgency). In this hypothetical example, it is especially advantageous for Petunia to get tested at an early stage because some promising new pharmaceutical compositions are being tested on human subjects, and these compositions are believed to have greater anti-PD efficacy if they are administered at an early stage of PD onset.

The PD detection rule discussed in the previous paragraph is triggered by a threshold number of transverse discontinuities per unit of swipe length. Alternatively, various rules may be triggered by other geometrical characteristics of a user's swipes, such as longitudinal distance between successive discontinuities (for example, are the discontinuities evenly spaced or do they come in clusters), angle of the transverse discontinuities (are they orthogonal to the longitudinal direction or skew to it), amplitude of the transverse discontinuities, whether transverse discontinuities are evenly distributed about the left and right sides of the longitudinal swipe path, longitudinal gaps in a swipe path, etc. In some embodiments of the invention, the gesture data analyzed is taken over a considerable time scale (which is facilitated by taking data during "normal operations" of a smart phone or tablet). Accordingly, different machine logic rules may account for time scale related issues in various ways. For example, some embodiments of the present invention might be able to distinguish, with some degree of confidence, between onset of PD and onset of Sundown Syndrome based upon how physical characteristics of gestures change (or don't change) with time of day. Alternatively, change detection module 312 could be programmed to examine different changes to gesture data sets (for example, the accuracy and quickness with which a stroke survivor navigates a touchscreen user interface).

Figure 4:
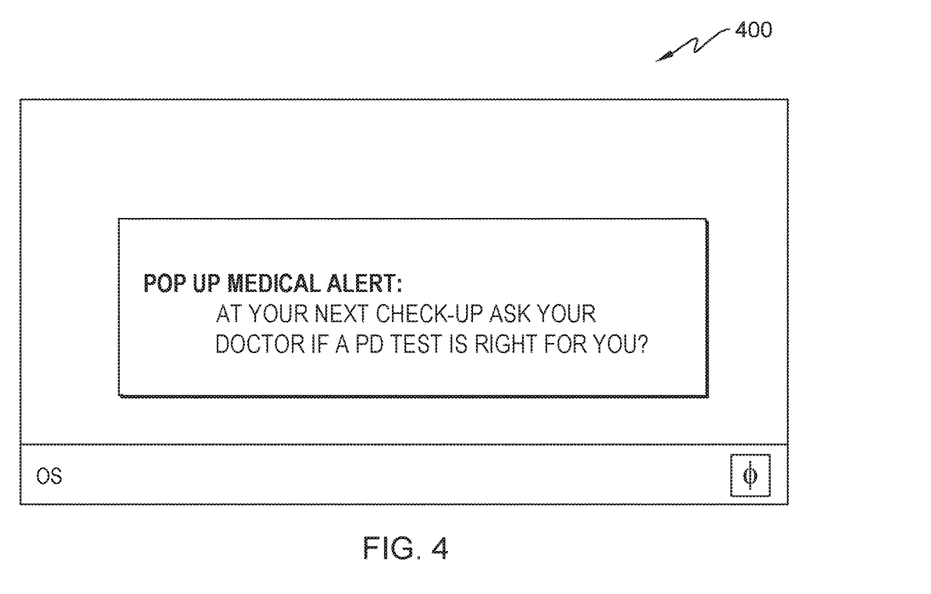
FIG. 4 is a screenshot view generated by the first embodiment system.

Processing proceeds to operation S275 where communication module 314 sends out a pop up medical alert to Petunia's computer device 106 as shown in FIG. 4. In this example, the reason that Petunia gets a pop up message, instead of an email is the relatively high urgency value of 0.75.

Processing proceeds to operation S280 where communication module 314 sends a communication over network 114 to Dr. Good's medical office's computer device 112 indicating that Petunia potentially has early onset of PD and suggests that Dr. Good may want to do a search for medical testing trials in which people who potentially are exhibiting onset of PD may participate. Alternatively, a message may be sent regarding different neurological phenomena (for example, to a client sub-system owned and operated by the parent of a child, informing them that their child's reading ability is behind expected levels and that additional hands-on time with the child or tutoring is recommended).

Processing proceeds to operation S285 where a physician administers a PD test to an individual under their care. In this example, Petunia schedules a PD screening test at Dr. Good's office and it is determined that she is likely coming to have PD. Alternatively, further tests based upon various indicator information generated by various embodiments of the present invention include further motor skills tests and/or further reading skills tests.

Processing proceeds to operation S290 where Dr. Good enrolls Petunia in a clinical trial of a promising new anti-PD drug.

III. Further Comments and/or Embodiments

Some embodiments of the present invention recognize the following facts, potential problems and/or potential areas for improvement with respect to the current state of the art: (i) due to different health conditions, some people may not be able to use the touch screen based devices very well; and/or (ii) it would be favorable if those conditions were detected early for treatment.

Some embodiments of the present invention may include one, or more, of the following features, characteristics and/or advantages: (i) information is collected through primary swipe finger's interaction with the touch screen; (ii) collection of historical data to determine the primary swipe finger and average pressure values a user (or group of users) uses to press on the screen; (iii) an invention system that can detect different condition changes through user's hand; (iv) pressure pattern changes on the touch screen based devices; (v) the information can be used for analyzing children fine motor skill changes, children reading level changes and/or Parkinson's disease detection; (vi) detection of other symptoms from the user such as sleeping cycle changes as the additional validations to determine whether the user has Parkinson's Disease; and/or (vii) to reduce the trail of errors, the invention system further detects the user's location/contextual environment/actions based on the user's calendar event data and GPS location data in order to determine whether the hands/fingers shaking behaviors were the results of nervousness or extensive physical exercises.

Some embodiments of the present invention may include one, or more, of the following features, characteristics and/or advantages: (i) the system is integrated with a pressure sensor on the user's touch screen based device (sometimes herein referred to as "prerequisites"); (ii) data detection stage: the user uses his/her fingers to swipe up and down to read the information; (iii) the system detects what is the user's commonly used primary finger to swipe the screen; (iv) the system detects, collects and calculates what is the user's general swiping speed and rhythm; (v) the system detects the user stopping and pressing hard on a certain area on the touch screen; (vi) the system detects the tip of the finger that pressed on the touch screen; (vii) the system compares the pressure currently pressed on the touch screen and the average pressure the user tends to press on the screen; and/or (viii) if the system determines the pressure is much harder than usual then the system records this information.

Figure 5:
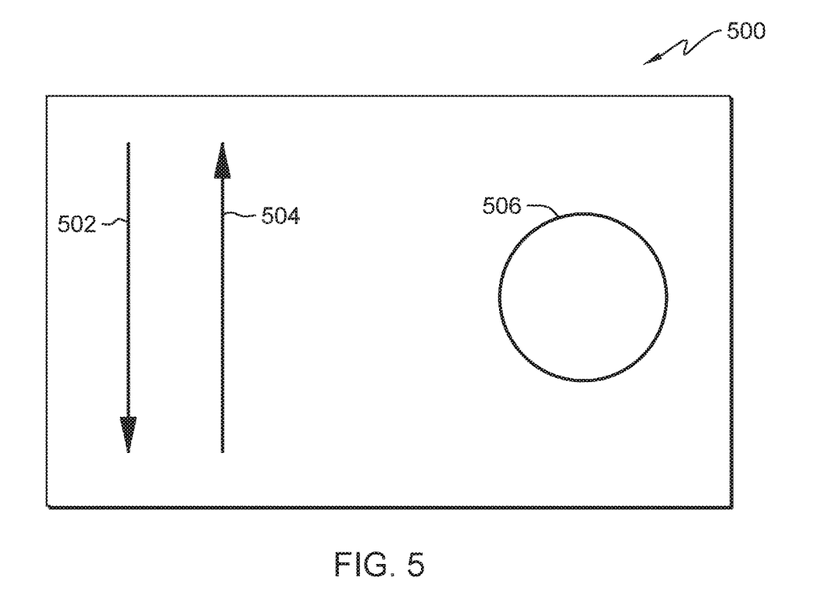
FIG. 5 is a screenshot view generated by an embodiment of the present invention.
Figure 6:
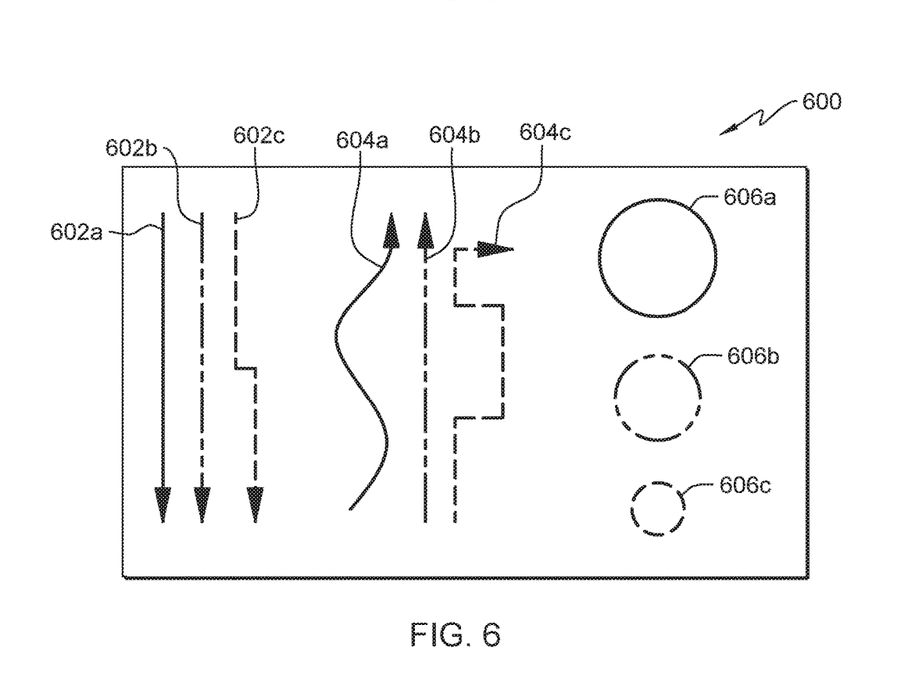
FIG. 6 is a screenshot view generated by an embodiment of the present invention.

Some embodiments convert the user's hand pressure, the trace of the finger swiping trace into digital representations such as the ones illustrated in screenshot 500 of FIG. 5 and screenshot 600 of FIG. 6. As shown in FIG. 5, screenshot 500 includes: first subject's downswipe path representation 502; first subject's upswipe path representation 504; and first subject's pressure level representation 506. More specifically, in this embodiment, the first subject's downswipe path representation, the first subject's upswipe path representation and the first subject's pressure level representation are gesture data when the subject is participating in "normal operations" (see definition in Definitions sub-section, below). Also, the swipe paths and pressure magnitude is an average collected over many separate upswipes, downswipes and taps.

In the embodiment of the present invention that generates screenshot 500, a straight vertical upswipe and a straight vertical downswipe is considered ideal from a neurological perspective, so down and upswipes 502, 504 are evidence that the first subject is not necessarily in need of an immediate neurological exam by a trained medical professional. Alternatively, in some embodiments, it may be determined that neurologically healthy people typically perform up and downswipes in patterns other than a straight line (for example, in the shape of a slight arc that is concave with respect to the direction of the subject's dominant hand). In these embodiments, the straight up and downswipes might indeed be an early indication of onset of a neurological condition that affects motor skills. As a further alternative, it may be determined that children typically change the pattern of vertical up and downswipes (or other gestures) as their brains develop and mature. In this kind of embodiment, straight, linear profile up and downswipes 504, 502 might mean that the child is at a stage of motor skill development typical of an eight year old (rather than a seven year old or a nine year old).

It is noted that tap pressure is represented as a circle in FIG. 5, but this can lead to confusion between pressure magnitude and the size of the area over which tap pressure is applied. In various embodiments of the present invention, either, or both, of these tap characteristics may be relevant.

As shown in FIG. 6, screenshot 600 includes: first subject's downswipe path representation 602a; second subject's downswipe path representation 602b; third subject's downswipe path representation 602c; first subject's upswipe path representation 604a; second subject's upswipe path representation 604b; third subject's upswipe path representation 604c; first subject's pressure level representation 606a; second subject's pressure level representation 606b; and third subject's pressure level representation 606c. In this embodiment, the identities of different subjects are represented by different line styles, but this can be represented other ways, such as by color coding.

In this embodiment, the first subject has a straight linear downswipe, but a wavy upswipe. In this hypothetical embodiment, it has been determined that many users exhibit this pattern, and it is not considered particularly indicative of any special physiological, developmental information of interest and/or neurological conditions.

In this embodiment, the second subject has a straight linear downswipe and upswipe. In this hypothetical embodiment, it has been determined that very few users actually exhibit this pattern (especially when they are not taking a dedicated hand gesture test). In this hypothetical, it has been determined that there is a strong correlation between this straight line swipe pattern and excellence in performing computer aided drafting (CAD). Furthermore, it is known that the second subject is enrolled in a mechanical engineering curriculum at a large public university. Therefore, the machine logic of the present invention sends the second subject a notification that she should consider enrolling in a CAD course offered by her university.

In this embodiment, the third subject has irregular downswipe and upswipe patterns. In this embodiment, this is not considered to be a problem in and of itself. For example, it may be that the third subject likes to participate in online chats while he rides the train. However, the third subject also has a very small tap pressure. In this embodiment, the irregular swipe patterns, taken in conjunction with a low tap pressure are considered as a possible indication of Amyotrophic Lateral Sclerosis. Therefore, the machine logic sends a notification to the third subject's doctor.

Some embodiments of the present invention may include one, or more, of the following features, characteristics and/or advantages: (i) data analysis stage: the system keeps finger trace and finger pressure related data along when the user presses hard on the screen; (ii) the system identifies to see whether there are big changes in the patterns; (iii) user's different fingertip tracing pattern and the fingertip pressure pattern will be recorded using a different color; (iv) some possible use cases for determining children's fine motor skill changes are as follows: (a) if the child starts with some rough finger swiping pattern trace but the trace gets smoother then the system record that positive trend, and (b) if the child can accurately tab on the touch screen more and more accurately on the fine points targets then the system can also record that positive trend; (v) when positive trends are going in parallel for a certain period of time then the system can conclude the child has continuously developed fine motor skills; (vi) in a children reading level changes use case, the child used to swipe the pages on touch screen based device slowly; (vii) the child is evaluated using the same level of reading material and he/she is able to swipe the pages faster now; and/or (viii) if the child can still answer the questions correctly after reading the text then it indicates the child has improved his reading skills within that reading level.

In a Parkinson's disease detection use case embodiment, the Parkinson's disease causes motor symptoms and non-motor symptoms. The most common one is tremor. If the user started to change the swiping pattern from a straight line to a dotted line and this pattern continues then this needs to be brought to the medical professional's attention.

In some embodiments, a systems determinations stage is as follows: the system can categorize the symptoms and associates the symptoms with the user profile data (age, medical history and etc.). The system can determine the potential cause of the symptoms based on the known scientific data.

Some embodiments of the present invention may include one, or more, of the following features, characteristics and/or advantages: (i) detection of other symptoms from the user such as sleeping cycle changes as the additional validations to determine whether the user has Parkinson's Disease; and/or (ii) to reduce the trail of errors, the invention system further detects the user's location/contextual environment/actions based on the user's calendar event data and GPS location data in order to determine whether the hands/fingers shaking behaviors were the results of nervousness or extensive physical exercises (for example, the user might be very nervous when presenting in front of a big crowd, the user's hands/fingers might shake a lot if the user just finishes some very intensive workout in the gym).

Some embodiments of the present invention may include one, or more, of the following features, characteristics and/or advantages: (i) monitoring a user's touch screen usage for pressure, speed, and usage context; (ii) analyzing the touch screen usage to determine a first pattern of usage in a first time frame; (iii) analyzing the touch screen usage to determine a second pattern of usage in a second time frame; (iv) comparing the second pattern of usage to the first pattern of usage to identify a change in pattern between the second time frame and the first time frame; (v) associating the change in the pattern with a change to the user; (vi) the change is an improvement based on learning; (vii) the change is a degradation attributed to a condition (for example Parkinson's, or children fine motor skill development); (viii) the change is a swiping pattern change; (ix) the change is a tabbing pattern change; (x) the change is a tracing pattern change; (xi) the change is a pressure pattern change; and/or (xi) determining a person's medical condition through detecting different types of pattern change of using a touched screen based device.

A goal of some embodiments the present invention is for detection of the PD (Parkinson's disease) candidates. It is known that people with Parkinson's disease shake or have tremors. Some embodiments of the present invention are based on the conjecture that this shaking or tremoring will show up in touchscreen swipe type gestures as an early sign of PD. It is understood that oncoming PD is not the only possible cause of shaky or jittery swipe gesture patterns. However, it is speculated that future analysis of the degree and/or nature of the pattern of the swipe gestures will be able to yield machine logic for separating early onset PD from other causes of gesture shakiness without too many Type II errors (that is, suggesting a PD test that turns out not to be helpful because there is no PD). Although it is probably acceptable if embodiments of the invention cause some Type II errors, it is understood that it would not be good if Type II errors heavily dominate the cases where an early indication of PD made by the present invention turns out to be correct.

Some embodiments of the present invention can be used for both general observation/detection for a child's reading development pattern as well as the case giving a child a reading test. A child is usually taught to put the finger right below the words he/she is reading. Some embodiments are based on the assumption that if a child can read continuously then the fingertip will leave a relatively smooth line on the touch screen based device.

IV. Definitions

Present invention: should not be taken as an absolute indication that the subject matter described by the term "present invention" is covered by either the claims as they are filed, or by the claims that may eventually issue after patent prosecution; while the term "present invention" is used to help the reader to get a general feel for which disclosures herein are believed to potentially be new, this understanding, as indicated by use of the term "present invention," is tentative and provisional and subject to change over the course of patent prosecution as relevant information is developed and as the claims are potentially amended.

Embodiment: see definition of "present invention" above—similar cautions apply to the term "embodiment."

and/or: inclusive or; for example, A, B "and/or" C means that at least one of A or B or C is true and applicable.

Including/include/includes: unless otherwise explicitly noted, means "including but not necessarily limited to."

Module/Sub-Module: any set of hardware, firmware and/or software that operatively works to do some kind of function, without regard to whether the module is: (i) in a single local proximity; (ii) distributed over a wide area; (iii) in a single proximity within a larger piece of software code; (iv) located within a single piece of software code; (v) located in a single storage device, memory or medium; (vi) mechanically connected; (vii) electrically connected; and/or (viii) connected in data communication.

Computer: any device with significant data processing and/or machine readable instruction reading capabilities including, but not limited to: desktop computers, mainframe computers, laptop computers, field-programmable gate array (FPGA) based devices, smart phones, personal digital assistants (PDAs), body-mounted or inserted computers, embedded device style computers, application-specific integrated circuit (ASIC) based devices.

Normal-operation touchscreen data set: any set of machine readable data that includes information indicative of one, or more, physical characteristic(s) of a gesture performed by a user where the gesture was performed in order to control operations of a program other than a program dedicated to making health-related recommendations or diagnoses; some typical normal operations are as follows: reading an electronic book through the touchscreen, emailing, chatting, making phone calls, controlling an audio player program, controlling a video player program, surfing the internet through a browser, storing media files in local or cloud storage, engaging in social media interactions, etc.

Physical characteristic(s) of a gesture: includes, but is not limited to hand pressure, swipe patterns, double tap interval, interval between flipping screens or scrolling data of an electronic text (for example, an electronic book), etc.

Gesture: any deliberate interaction between a user's hand and a touchscreen input device; "gesture swipe" is a kind of gesture where the user drags a fingertip across the surface of a touchscreen (for example, straight line gesture wipe, looping continuous gesture swipe (for cursive "handwriting," for example)).

Health-related recommendation: any communication including information relating to a physical and/or mental condition of a human user; does not have to be related to disease or illness; for example, a message that says that "User A has a beautiful reading ability relative to her age" is considered as an example of a health-related recommendation.

Medical entity: any person, business, or organization that provides medical or medical related services including, but not limited to: a physician, a specialist healthcare provider (for example, a neurologist, occupational therapist, hand surgeon, or developmental pediatrician), pharmacist, clinic, medical practice, hospital, health insurance provider, pharmaceutical company, medical educational facility, medical device developer, or health directed government agency (for example, the National Institutes of Health).

What is claimed is:

1. A computer-implemented method for use with a pressure sensitive touchscreen user interface device, the method comprising:
    receiving a Parkinson's Disease (PD) potential indication module including a set of machine logic based rules for determining when changes in gesture pressure patterns of touchscreen gesture instances correspond to a potential indication of early onset of PD;
    receiving a plurality of touchscreen gesture data sets, with each touchscreen gesture data set including information indicative of: (i) pressure levels throughout an instance of a gesture swipe made by a user on the pressure sensitive touchscreen user interface device, and (ii) a time that the instance of the touchscreen gesture swipe occurred;
    detecting a first change in pressure levels throughout the user's gestures over time by comparing touchscreen gesture data sets of the plurality of touchscreen gesture data sets with each other;
    applying the machine logic based rules of the PD potential indication module to determine that the detection of the first change in pressure corresponds to a potential indication of PD;
    accessing location data for the pressure sensitive touchscreen user interface device;
    modifying results of the application of the machine logic based rules of the PD potential indication module based, at least in part, on the accessed location data for the pressure sensitive touchscreen user interface device, and
    sending a communication indicating a potential indication of PD for the user.

2. The computer-implemented method of claim 1 wherein the first change in pressure levels is indicative of smaller handwriting.

3. The computer-implemented method of claim 1 wherein the first change in pressure levels is indicative of tremors.

4. The computer-implemented method of claim 1 wherein the first change in pressure levels occurs over a period that is greater than a month.

5. The computer-implemented method of claim 1 wherein the communication is sent to the user.

6. The computer-implemented method of claim 1 wherein the communication is sent to a medical entity.

7. A computer program product (CPP) for use with a pressure sensitive touchscreen user interface device, the CPP comprising:
    a machine readable storage device; and
    computer code stored on the machine readable storage device, with the computer code including instructions for causing a processor(s) set to perform operations including the following:
        receiving a Parkinson's Disease (PD) potential indication module including a set of machine logic based rules for determining when changes in gesture swipe pressure patterns of touchscreen gesture instances correspond to a potential indication of early onset of PD, receiving a plurality of touchscreen gesture data sets, with each touchscreen gesture data set including information indicative of: (i) pressure levels throughout an instance of a gesture made by a user on the pressure sensitive touchscreen user interface device, and (ii) a time that the instance of the touchscreen gesture swipe occurred, detecting a first change in pressure of the user's gestures over time by comparing touchscreen gesture data sets of the plurality of touchscreen gesture data sets with each other, applying the machine logic based rules of the PD potential indication module to determine that the detection of the first change in pressure corresponds to a potential indication of PD, accessing location data for the pressure sensitive touchscreen user interface device;

modifying results of the application of the machine logic based rules of the PD potential indication module based, at least in part, on the accessed location data for the pressure sensitive touchscreen user interface device, and sending a communication indicating a potential indication of PD for the user.

8. The CPP of claim 7 wherein the first change in pressure is indicative of smaller handwriting.

9. The CPP of claim 7 wherein the first change in pressure is indicative of tremors.

10. The CPP of claim 7 wherein the first change in pressure occurs over a period that is greater than a month.

11. The CPP of claim 7 wherein the communication is sent to the user.

12. The CPP of claim 7 wherein the communication is sent to a medical entity.

13. A computer system (CS) for use with a pressure sensitive touchscreen user interface device, the CS comprising:
   a processor(s) set;
   a machine readable storage device; and
   computer code stored on the machine readable storage device, with the computer code including instructions for causing the processor(s) set to perform operations including the following:
   receiving a Parkinson's Disease (PD) potential indication module including a set of machine logic based rules for determining when changes in gesture pressure patterns of touchscreen gesture instances correspond to a potential indication of early onset of PD,
   receiving a plurality of touchscreen gesture data sets, with each touchscreen gesture data set including information indicative of: (i) pressure levels throughout an instance of a gesture made by a user on the pressure sensitive touchscreen user interface device, and (ii) a time that the instance of the touchscreen swipe occurred,
   detecting a first change in pressure of the user's gestures over time by comparing touchscreen gesture data sets of the plurality of touchscreen gesture data sets with each other,
   applying the machine logic based rules of the PD potential indication module to determine that the detection of the first change in pressure corresponds to a potential indication of PD,
   accessing location data for the pressure sensitive touchscreen user interface device;
   modifying results of the application of the machine logic based rules of the PD potential indication module based, at least in part, on the accessed location data for the pressure sensitive touchscreen user interface device, and
   sending a communication indicating a potential indication of PD for the user.

14. The CS of claim 13 wherein the first change in pressure is indicative of smaller handwriting.

15. The CS of claim 13 wherein the first change in pressure is indicative of tremors.

16. The CS of claim 13 wherein the communication is sent to the user.

17. The CS of claim 13 wherein the communication is sent to a medical entity.

* * * * *